US008622909B1

(12) United States Patent
O'Ruanaidh et al.

(10) Patent No.: US 8,622,909 B1
(45) Date of Patent: *Jan. 7, 2014

(54) METHOD OF LOCATING THE POSITION OF A MICROCALCIFICATION IN A HUMAN BREAST

(75) Inventors: Joseph J. O'Ruanaidh, Hamilton, NJ (US); Christopher J. Vecchio, Philadelphia, PA (US); Edmond Rambod, Los Angeles, CA (US)

(73) Assignee: Quantason, LLC, Los Angeles, CA (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/925,378

(22) Filed: Oct. 19, 2010

(51) Int. Cl.
  *A61B 8/00* (2006.01)
(52) U.S. Cl.
  USPC .......................................... 600/437; 600/407
(58) Field of Classification Search
  USPC .......................................... 600/407, 437–472
  See application file for complete search history.

(56) References Cited

U.S. PATENT DOCUMENTS

2002/0065466 A1* 5/2002 Rather et al. .................. 600/447
2009/0247869 A1* 10/2009 Rambod et al. ............... 600/437

OTHER PUBLICATIONS

Zemp, Roger. Detection Theory in Ultrasonic Imaging. 2004. University of California Davis. pp. 1-229 (and preface).*
PCT/US2007/061045, 2006, O'Ruanaidh.
G. Bretthorst, Spectrum Ahalysis and Parameter Estimation (Springer Verlag 1989).
J.J.K.O Ruanaidh and W.J. Fitzgerald, Numerical Bayesian Methods Applied to Signal Processing (Springer Verlag, 1996).
W. Press, S. Teukolsky, W. Vetterling and B. Flannery Numerical Recipes in C (Cambridge University Press, 1992), 2nd ed.
A. Quinn and M. MacLeod, "The distinction between joint and marginal estimators" in Fourth Valencia International Meeting on Bayesian Statistics (1991).
A. Quinn, "The performance of Bayesian estimators in the super-resolution of signal parameters," in "IEEE International Conference on Acoustics, Speech and Signal Processing" (1992).
A. Quinn, "Bayesian point inference in signal processing," Ph.D. thesis, Cambridge University Engineering Department, England (1992).
M. Tanner, Tools for Statistical Inference (Springer Verlag, 1993).
S. Haykin, Communication Systems (NY: Wiley, 1994) 3rd ed.

* cited by examiner

*Primary Examiner* — James Kish
(74) *Attorney, Agent, or Firm* — Thomas I. Rozsa

(57) ABSTRACT

This invention relates to diagnostic and screening medical ultrasound in general and to ultrasound-stimulated detection and location, Image-based Dynamic Ultrasound Spectrography, Acoustic Radiation Force Imaging, and similar modalities in particular. In this invention, an ultrasound signal is emitted into tissue and the resulting radiation force induces localized lower frequency oscillations, which are then received by various acoustic sensors and analyzed to determine certain features or characteristics of the interrogated region. The sensors can be arranged in the form of a ring, in any random arrangements, or positioned in specifically chosen locations. An ultrasonic imaging and excitation transducer generates certain stimulating signals which are received by the breast tissues and which, if they contact a microcalcification, other target, or any region with sharply different mechanical and visco-elastic properties, will result in reflected, demodulated, or re-radiated signals. These signals will propagate away from the targets and detected by the various receiving sensors.

29 Claims, 4 Drawing Sheets

METHOD OF LOCATING THE POSITION OF A MICROCALCIFICATION IN A HUMAN BREAST

BACKGROUND OF THE INVENTION

1. Field of the Invention

The present invention relates to the detection and location of microcalcifications in the human breast with a view to detecting and treating malignant cancer at an early stage.

2. Description of Prior Art

Breast cancer is often characterized by the presence of calcifications along mammary ducts. These may be detected using X-ray mammography. Mammograms do have a number of drawbacks. First, calcifications appear as white objects. Fibroglandular tissue, which is normal in breasts, also appears as white which leads to poor contrast in mammogram images. Second, a mammogram is an extremely uncomfortable procedure. Third, mammography is an X-ray based modality which involves exposure to potentially harmful ionizing radiation. An alternative approach, which does lead to better image quality and diagnosis, is to use magnetic resonance imaging (MRI). However, MRI is prohibitively expensive and could be out of reach for all but limited number of patients with certain socioeconomic standing.

The concept of using ultrasound technology to detect and locate calcifications has in general been developed prior to this invention. The benefit of using ultrasound is that it is portable, relatively cheap and does not expose the patient to harmful radiation. Moreover, in cases with dense breasts, mammograms have proven useless and thus, ultrasound is the only method of choice, next to expensive and unaffordable MRI.

One of the current inventors, Dr. Edmond Rambod, has developed the concept of using ultrasound in conjunction with four or more microphones or sensors located on a ring— or other sensor housing configurations—which is positioned on or around the breast. The acoustic sensors are meant to detect sound radiation radiated from a stimulated target. Since the speed of sound is constant and finite, the signal will arrive at each of the sensors at a different time. If one can precisely estimate the time delays at each sensor then, in theory, one can locate the location of the target. According to Dr. Rambod's invention, a conventional ultrasound transducer (imager or scanner) is used to deliver certain acoustic force to a target and thus, excite a source of acoustic radiation such as a microcalcification. The resulting sound signals are then received by the sensors. Analysis of the data acquired by the sensors and use of certain location paradigms will allow one to determine the location of the target (i.e., microcalcification in the human breast). The inventors of the present invention, including Edmond Rambod, have determined that there is an accurate way to determine the location of an acoustic radiation source such as a microcalcification in a human breast in order to facilitate its classification, biopsy or removal if the microcalcification is proven to be associated with cancer. The following prior art technology is utilized in the present invention:

[1] G. Bretthorst, *Bayesian Spectrum Analysis and Parameter Estimation* (Springer Verlag, 1989).
[2] J. J. K. Ó Ruanaidh and W. J. Fitzgerald, *Numerical Bayesian Methods Applied to Signal Processing* (Springer Verlag, 1996).
[3] W. Press, S. Teukolsky, W. Vetterling, and B. Flannery, *Numerical Recipes in C* (Cambridge University Press, 1992), 2nd ed.
[4] A. Quinn and M. MacLeod, "The distinction between joint and marginal estimators" in "Fourth Valencia International Meeting on Bayesian Statistics" (1991).
[5] A. Quinn, "The performance of Bayesian estimators in the superresolution of signal parameters," in "IEEE International Conference on Acoustics, Speech and Signal Processing" (1992).
[6] A. Quinn, "Bayesian point inference in signal processing," Ph.D. thesis, Cambridge University Engineering Department, England (1992).
[7] M. Tanner, *Tools for Statistical Inference* (Springer Verlag, 1993).
[8] S. Haykin, *Communication Systems* (NY: Wiley, 1994), 3rd ed.
[9] J. J. K. Ó Ruanaidh, Y. Zhang, P. Emeric, M. R. Swiatek and V. Rozenfeld, "System and method for providing an optical section image by direct phase angle determination and use of more than three images", U.S. patent application Ser. No. 11/341,935 PCT/US2007/061045 (2006).

SUMMARY OF THE INVENTION

This invention relates to diagnostic and screening medical ultrasound in general and to ultrasound-stimulated detection and location, Image-based Dynamic Ultrasound Spectrography (IDUS), Acoustic Radiation Force Imaging (ARFI), and similar diagnostic and screening imaging modalities in particular. In these imaging modalities an ultrasound signal is emitted into tissue and the resulting radiation force induces localized lower frequency oscillations (vibrations). These vibrations are then received and analyzed to determine or detect certain features or characteristics of the interrogated region. The IDUS medical imaging modality relies on an array of acoustic sensors placed around or adjacent to a human breast or other part of the body. The sensors can be arranged in the form of a ring, can be in any random arrangement of locations, or can be positioned in specifically chosen locations. The sensors can all be located in the same plane or in any 3-dimensional configuration. An ultrasonic imaging and excitation transducer generates certain stimulating signals which are received by the breast tissues and which, if they contact a microcalcification, other target, or any region with sharply different mechanical and visco-elastic properties, will result in reflected, demodulated, or re-radiated signals. These signals will propagate away from the microcalcification or other targets and can be detected by the various receiving sensors.

The present invention is a method whereby one can locate such a target based on an analysis of its emitted acoustic signals. The emitted signals can be, for example, longitudinal waves of relatively high speed (e.g. 1480 meters/sec in breast tissue, fat, etc) or transverse waves of generally slow sound speeds (on the order of 10 meter/sec or less in biological tissue). The corresponding phase differences induced by travel time delay from the source to the sensor may be quite small, particularly at low frequencies. It is generally believed by those skilled in the art that these phase differences are too small to be of valuable use in locating the target. Contrary to general belief, in the present invention, it has been discovered that the method is precise enough to yield phase estimates that can be used to reliably locate a target (i.e., calcification).

The steps are:
1) An optional preliminary spectral analysis step to determine frequency and/or chirp and/or other non-linear parameters contained in the regression matrix. This step is optional because these values are typically known in advance.

2) Regression to estimate the magnitude of in-phase and quadrature components. Linear regression is typically used in this step but it will be evident to those skilled in the art that robust regression can be substituted for linear regression and may yield better results in some circumstances. Moreover, we also recognize that Bayesian regression can also be applied to utilize prior information about the linear parameters.
3) Phase estimation calculated directly from the linear parameters using a standard formula.
4) Conversion of the phase estimates into a position estimate using non-linear optimization of a cost function.

The present invention also derives estimates for the phase standard deviation. This expression follows from a standard propagation-of-errors argument that would be familiar to those skilled in the art. Nonetheless, the original application of these quantities is used for measuring objectively the quality of the data gathered by a specific sensor. These quantities are also useful in devising the cost function, the minimization of which yields an estimate of the location of the source of acoustic radiation.

In addition, the present invention describes a maximum likelihood approach to target location. Furthermore, the present invention method can also be used to optimize the location of the sensors. This goal can be attained by optimizing the position of the sensors with respect to a cost function. In this configuration, the true location of the target would be known and those positions of the acoustic sensors that yield the best estimate of the true location would be considered optimal. The true location would be determined over a suitably large number of trials in which the true target location would be chosen either judiciously, or randomly, or some combination thereof in an effort to be representative of the target locations in a real-world situation (i.e., inside of the human breast relative to sensors positioned on the body surface on or around the breast).

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
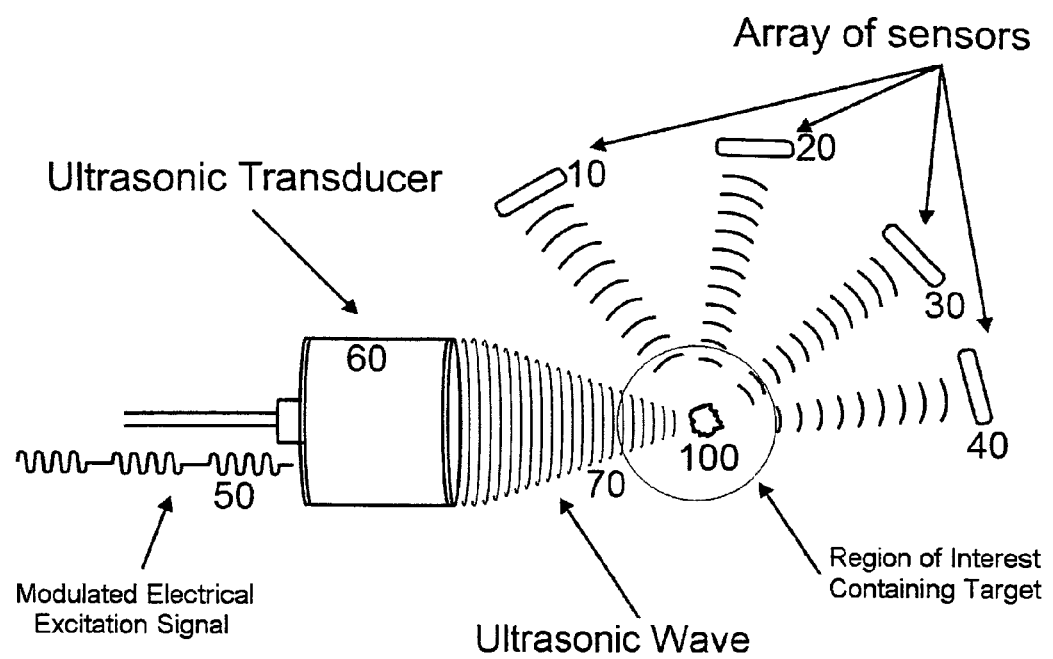
FIG. 1 is a diagram showing a single element ultrasonic transducer applying a modulated radiation force, or a modulated ultrasound signal, or a modulated beam of ultrasound wave energy to a target in a medium such as biological tissue and the reception of the resulting demodulated signals by an array of acoustic sensors.

Although specific embodiments of the presented invention are described herein with reference to the drawings, it should be understood that such embodiments are by way of example only. They merely illustrate but a small number of the many specific embodiments which can represent applications of the principles of the present invention. Various changes and modifications, obvious to one skilled in the art, to which the present invention pertains, are deemed to be within the spirit, scope and contemplation of the present invention as further defined in the appended claims.

The initial concept of the present invention is to introduce a multiplicity of acoustic sensors at given locations on or around or adjacent to a human breast. When used in this application, the term "sensor" applies to an acoustic sensor and "acoustic sensor" can include the following: a microphone, microphones, a hydrophone, hydrophones, an accelerometer, accelerometers, a strain gauge, strain gauges, a surface microphone, surface microphones, a surface hydrophone and surface hydrophones. It is understood that when the term "sensor" is set forth in this application, it includes all of the above.

The sensors can be arranged in the form of a ring, can be in any random arrangement of locations, or can be positioned in specifically chosen locations. The sensors can all be located in the same plane or in a 3-dimensional configuration on or around a human breast. An ultrasound transducer or a conventional ultrasound imaging transducer (also referred to as imager or scanner) scans the breast to generate a B-mode gray-scale image of the whole breast or certain segments of the breast (also referred to as quadrants) and either simultaneously or sequentially to formation of the B-mode image, transmits certain stimulating signals to the scanned area of the breast which are received by all the layers of the breast and which, if they impact a calcification or microcalcification or other target in the breast, will result in reflected, demodulated, or reradiated signals from the said calcification or microcalcification or other target. These reflected, demodulated or reradiated signals will travel away from the calcification, microcalcification or other target and toward a location or locations where the various sensors are positioned on or around the human breast.

A real-time phase analysis of the information received by each sensor can be carried out in order to determine the location of the radiating target (i.e., calcification or microcalcification). Because each sensor is located at a slightly different distance from said target, the different distances result in different phase shifts in the signals received by each sensor.

The phase shifts are proportional to the distance between each sensor and the radiating target. The phase shifts correspond to the time between the generation of the ultrasonic stimulation signal and the reception by the sensor of a resulting signal reflected, demodulated, or reradiated by the target. If the time at which the stimulation signal is generated is known (and used as a reference) and the location of the stimulation transducer and each of the receiving sensors is known, then the location of the target may be determined relative to that of the sensors.

Referring to FIG. 1, which depicts four sensors 10, 20, 30 and 40, positioned at various locations and modulated electrical excitation signals 50, and a transducer 60 generating stimulating acoustic waves 70 impacting a tissue with a microcalcification which is designated as the target 100 and which reflects, reradiates, or demodulates the signals from the transducer and thereby generates emitted signals to be received by the four sensors. The concept is that the time it takes for a signal to travel between the stimulated target, or stimulated microcalcification within the tissue, and each of the four sensors depends on the distance between the specific sensor and the stimulated microcalcification within the tissue. If these signal travel times are known, and the locations of the sensors and stimulating transducer are known, then one can locate the position of the microcalcification within the tissue.

The present invention uses the following notation. Matrices and vector quantities are written in bold face. Examples include:

d: an N×1 vector consisting of N data points;
G: an N×M matrix consisting of M columns often referred to as a "regression matrix" in the literature;
c: an M×1 matrix of parameters; and
e: N×1 vector consisting of N data points, comprising the error in fitting the data.

Scalar quantities are written in plain text. An element of a vector is written with a subscript (for example: $d_i$.). In addition, the standard practice of writing mathematical variables in italics is practiced.

The first element of the present invention is the "phase estimation method". The key challenge in implementing this method is to estimate $\phi_1$, $\phi_2$, $\phi_3$ and $\phi_4$ at each one of the sensors in FIG. 1. Received data are of the following form:

$$d_i = A\cos(\omega t_i + \phi_i)e^{-\beta l_i} + e_i \qquad \text{Equation (1)}$$

where, $$e_i \sim N(0, \sigma^2)$$

is a noise component drawn from a Gaussian distribution with mean zero and variance $\sigma^2$, $\omega$ is the frequency of the received signal, and $\beta$ is the attenuation of the material applied over the distance $l_i$ between the stimulated target and the respective receiving sensors for $i \geq 3$.

From basic physics, one may derive that:

$$\delta_i = \frac{\phi_i}{\omega} = \frac{l_i}{c} \qquad \text{Equation (2)}$$

where $\delta i$ is the time delay, $l_i$ is the distance between the stimulated target and the respective receiving sensors, $\phi_i$ is the phase, and c is the speed of sound.

The exponential term is of no real importance in what follows. In theory, one could use this information to estimate $\beta$ and $l_i$, thus obtaining a source of data to infer position. The present invention improves upon this basic approach by utilizing phase shifts determined by Bayesian spectral estimation as our primary source of information to infer position.

For the present invention, a sinusoidal waveform of frequency $\omega$ varying in time may be represented as:

$$d_i = a\cos(\omega t_i) + b\sin(\omega t_i) + \mu + e_i \qquad \text{Equation (3)}$$

where a is the in-phase amplitude, b is the quadrature amplitude, $\mu$ is the mean offset and $e_i$ is normally distributed zero mean noise. The phase is given simply by:

$$\tan\phi = -\frac{b}{a}$$

and the magnitude by:

$$A = \sqrt{a^2 + b^2}.$$

This model is equivalent to that in Equation 1.

A standard method of spectral analysis using the Fast Fourier Transform (FFT) in combination with data windowing and zero padding is not optimal. As set forth in known references, there are deficiencies in using FFT which include but are not limited to:

Limited precision because of discrete valued frequencies;
Reliance on ad hoc methods such as data windowing;
Difficulty in working directly with "wrapped around" phase of the FFT.

Following one of the present inventors, Joseph Ó Ruanaidh, Equation 3 may be rendered in an expanded form, $$d = Gc + e,$$

if there is a single transducer generating or inducing the signals received by a multiplicity of sensors. Note: bold face type is used to indicate matrices. The fully expanded equation is:

$$\begin{bmatrix} d_1 \\ d_2 \\ d_3 \\ \vdots \\ d_N \end{bmatrix} = \begin{bmatrix} \cos\omega t_1 & \sin\omega t_1 & 1 \\ \cos\omega t_2 & \sin\omega t_2 & 1 \\ \cos\omega t_3 & \sin\omega t_3 & 1 \\ \vdots & \vdots & \vdots \\ \cos\omega t_N & \sin\omega t_N & 1 \end{bmatrix} \begin{bmatrix} a \\ b \\ \mu \end{bmatrix} + \begin{bmatrix} e_1 \\ e_2 \\ e_3 \\ \vdots \\ e_N \end{bmatrix} \qquad \text{Equation (4)}$$

Equation 4 is the starting point for applying Bayesian analysis for phase estimation, which is used in this invention for locating the signal emitting target.

The likelihood function for the four parameters: (A) in-phase amplitude, (B) quadrature amplitudes (i.e., amplitude of the cosine and sine components), (C) noise variance, and (D) the frequency of the grid, is given in Equation 5:

$$p(d \mid a, b, \sigma, \{\omega\}) = p(e) = \qquad \text{Equation (5)}$$

$$\prod_{i=1}^{N} \frac{1}{\sqrt{2\pi\sigma^2}} \exp\left[-\frac{e_i^2}{2\sigma^2}\right] = (2\pi\sigma^2)^{-N/2} \exp\left[-\frac{\sum_{i=1}^{N} e_i^2}{2\sigma^2}\right]$$

From this one can derive the marginal probability density for the angular frequency $\omega$, which is given by Equation 6:

$$p(\{\omega\} \mid d, I) \propto |G^T G|^{-1/2} [d^T d - f^T f]^{-(N-3)/2} \qquad \text{Equation (6)}$$

where I denotes "prior information" (the state of knowledge that led to the selection of this model), and $$f = G(G^T G)^{-1} G^T d$$

is the least squares fit to the data d. Equation 6 described a student t-distribution with N−3 degrees of freedom (see Ó Ruanaidh and Fitzgerald [2]). This function is a one dimensional continuous function of the angular frequency ω and, compared to the full likelihood function, is relatively easy to optimize. In this scheme, the other parameters are treated as "nuisance parameters" and have been integrated out.

Working with log p({ω}|d, I) for convenience (p({ω}|d, I) has a very large range of positive values), one may compute the log probability for discrete values of ω over an interval to find the approximate location of the largest peak. Then, the present invention improves upon this initial estimate by using a non-linear optimization technique such as Brent's method, to locate the global maximum accurately. Once the extremum is found, the parameters c=(a, b, μ) can be estimated by linear regression as:

$$\hat{c} = (G^T G)^{-1} G^T d$$

where, $$G = G(\hat{\omega})$$

is a matrix function of the estimated value of ω and the phase values for each sensor can be calculated as:

$$\tan\phi_i = -\frac{b_i}{a_i}$$

Because the parameters are not estimated jointly, as in a typical maximum likelihood estimator, but rather are estimated sequentially, this estimator is not strictly optimal. However, this particular estimator using Bayesian estimators is supported in the literature and in prior art as being accurate. The differences between joint and marginal estimates are exceedingly minute and are not significant in this particular application.

In the present invention, it should not normally be necessary to estimate ω because it is already known. It would only be necessary to estimate it if the "known" value is inaccurate. At the very least, the present invention uses certain prior knowledge of ω (developed by the inventors) as a starting point for the optimization search which yields values for both ω and each $\phi_i$.

Following the phase estimation using Bayesian analysis, an error analysis is then needed in order to assess the accuracy of the phase estimates. The accuracy analysis proceeds as follows: The covariance matrix of the parameters a and b, derives from the Hessian matrix of the log likelihood function as identified by M. Tanner (Reference 7) and comprises the 2×2 partition of the 3×3 matrix:

$$C_{a,b,\mu} = \sigma^2 (G^T G)^{-1} \qquad \text{Equation (7)}$$

The Jacobian of transformation J between the Cartesian coordinates (a, b) and the polar coordinates (r, φ) is:

$$J = \begin{bmatrix} \frac{\partial r}{\partial a} & \frac{\partial r}{\partial b} \\ \frac{\partial \phi}{\partial a} & \frac{\partial \phi}{\partial b} \end{bmatrix} = \frac{1}{r}\begin{bmatrix} a & b \\ -\frac{b}{r} & \frac{a}{r} \end{bmatrix} \qquad \text{Equation (8)}$$

where, $$\tan\phi = -\frac{b}{a}$$

and $$r = \sqrt{a^2 + b^2}$$

According to the method of propagation of errors:

$$C_{r,\phi} = J C_{a,b} J^T \qquad \text{Equation (9)}$$

The variance of the phase estimate is given by the second diagonal element of the covariance matrix. This approximates the minimum variance that any statistical estimate, derived with the model assumptions used by the present invention can attain; namely, the Cramer-Rao bound (see Reference 8).

The model as set forth in Equation 4 deals with the case of a single stimulation frequency being transmitted to the target. It is also possible to use a multi-chromatic stimulation signal such as a chirp or chord instead of a single frequency. In fact in the application of detection and location of microcalcification in the breast tissue, it may be advantageous for an excitation signal to contain a range of frequencies because the response of targets to different stimulation frequencies depends on their physical size and density which are not known in advance and also because a non-monochromatic excitation may be more robust in the presence of standing waves or other interference. It should therefore be noted that the analysis above may be generalized to apply to any excitation waveform since any band-limited real waveform may be described by a linear superposition of monochromatic components. Application of the approach to the case of a linear chirp is shown for example below.

The data gathered by the receiving acoustic sensors in response to the stimulation of the target by a multiplicity of chirp signals are set forth in the following Equation 10:

$$\begin{bmatrix} d_1 \\ d_2 \\ d_3 \\ \vdots \\ d_N \end{bmatrix} = \begin{bmatrix} \cos(\alpha t_1^2 + \omega t_1) & \sin(\alpha t_1^2 + \omega t_1) & 1 \\ \cos(\alpha t_2^2 + \omega t_2) & \sin(\alpha t_2^2 + \omega t_2) & 1 \\ \cos(\alpha t_3^2 + \omega t_3) & \sin(\alpha t_3^2 + \omega t_3) & 1 \\ \vdots & \vdots & \vdots \\ \cos(\alpha t_N^2 + \omega t_N) & \sin(\alpha t_N^2 + \omega t_N) & 1 \end{bmatrix} \begin{bmatrix} a \\ b \\ \mu \end{bmatrix} + \begin{bmatrix} e_1 \\ e_2 \\ e_3 \\ \vdots \\ e_N \end{bmatrix} \qquad \text{Equation (10)}$$

where, as previously, noise is assumed to be Gaussian zero mean noise of variance $\sigma^2$. The only difference between Equation 4 and Equation 10 is that the single frequency ω in Equation 4 has been replaced by two parameters; initial frequency ω and linear chirp rate 2α in Equation 10. Note, linear chirp implies frequency increases linearly with time as ω+2αt, therefore the phase above is: $\omega t + \alpha t^2$. Using two parameters instead of just one means that a more general numerical optimization search is required to determine both the initial frequency, ω (the frequency when t=0), and the linear chirp rate 2α. But, as before, the initial frequency and chirp should be known from the experimental procedure. It should be noted that, for a given time delay between the same signal from the target to be received by the multiplicity of sensors, the phase shift depends on the frequency. In Equation 2, ω is the initial frequency, where t=0.

Applying the Bayesian analysis as before to this system of equations, yields a set of estimates for the phase at each of the sensors. With this information, one can convert the relative phases into a location of the target using the steps below.

The location of the source of acoustic radiation is mathematically equivalent to finding the point of intersection between a number of ellipsoids, each of which has one focus located at the excitation transducer, the other focus centered on a particular sensor, and a major diameter determined by the phase shift of the signal received by that sensor relative to the excitation waveform. This phase shift corresponds to the time between the generation of the ultrasonic excitation signal and the reception by the sensor of a signal reflected, demodulated, or reradiated by the target.

The process of determining the location of a target, in three dimensions, from its known distance from a set of other points is known as trilateration. This is distinct from triangulation, which is a very commonly used term, but which strictly speaking, only applies to determining location using angles. The general process of determining location from distance in any arbitrary number of dimensions is known as multilateration.

The approach used here to solve the multilateration problem is to optimize a cost function. The present invention is aimed at determining the position x of the target which, overall, best explains the data. For each sensor, there is the following relation:

$$|x|_2 + |x - p_i|_2 = c\Delta t_i = c\frac{\phi_i}{2\pi}T \quad \text{Equation (11)}$$

where $p_i$ is the location of the sensor and x is the position of the target, $\Delta t_i$ is the time of propagation and c is the speed of sound. The location of the transducer is at origin. The $|\cdot|_2$ operator around $x-p_i$ is the 2-norm, or Euclidean norm, computed as the square root of the sum of each component squared. This is the most commonly used measure of the length of a vector. For example, $|(-3, 4, -12)|_2=13$.

The present invention defines a cost function as follows:

$$C(x) = \sum_{i=1}^{M} \frac{||x|_2 + |x - p_i|_2 - c\Delta t_i|_1}{\sigma_{\phi_i}^2} \quad \text{Equation (12)}$$

where M is the number of sensors and the $|\cdot|_1$ operator is the 1-norm, or Manhattan norm, computed as the sum of the absolute values of each component. An example of 1-norm is $|(-3, 4, -12)|_1=19$. The 1-norm is used here because it yields a more robust estimator than summing squares. The 2-norm may also be used. The individual contribution from each sensor is weighted by the variance of the phase.

The best estimate for x is that which minimizes the cost function. The minimum possible value of the cost function is zero, which in real terms would correspond to locating the target exactly. In real data, however, the cost function is always greater than zero because of noise.

Therefore, the concept is to have an iterative process of systematically changing x in order to lower the value of the cost function, until the cost function is zero or as close to zero as can be obtained. When the cost function is zero or as close to zero as possible, then the most precise value for x in the equation 12 has been determined and that will determine the three-dimensional position coordinate of the vector x (i.e. the location of the target relative to the position of the sensors) so that the location of the microcalcification in the breast tissue can be ascertained.

Another cost function can also be described as the negative of a log likelihood function that takes in to account path dependent delays and phase changes. The following expression is the log likelihood function for the target being at position T.

$$\log p(d \mid x = T) = -\frac{N-M}{2}\sum_{i=1}^{L}\log[d_i^T d_i - d_i^T G_i (G_i^T G_i)^{-1} G_i^T d_i]$$

The contribution of each path to the log likelihood is in the form of a student t-distribution like Equation (6). In deriving this result, the nuisance parameters (namely the standard deviation σ and the linear parameters) are assumed to be different for each path. The model matrix G is also path dependent. L is the number of sensors which is equal to the number of paths. M is the number of columns in the matrix G. N is the number of rows in the matrix G.

In the general case, if the emitted signal is f(t) then the path dependent model matrix is:

$$G_i = \begin{bmatrix} 0 \\ 0 \\ \vdots \\ f(kT - \delta_i) \\ f((k+1)T - \delta_i) \\ f((k+2)T - \delta_i) \\ \vdots \\ f(NT - \delta_i) \end{bmatrix}$$

where, δi is the path delay and T is the sample period. The leading zeros are present because no signal can possibly be received before the time-of-flight has elapsed.

In the specific case where the emitted signal is cos(ωt) then the path dependent model matrix is:

$$G_i = \begin{bmatrix} 0 \\ 0 \\ \vdots \\ \cos\left(\omega(kT) - \frac{\rho_i}{c}\right) \\ \cos\left(\omega((k+1)T) - \frac{\rho_i}{c}\right) \\ \cos\left(\omega((k+2)T) - \frac{\rho_i}{c}\right) \\ \vdots \\ \cos\left(\omega(NT) - \frac{\rho_i}{c}\right) \end{bmatrix}$$

where ρi is the distance from source to sensor (via the target) along the path. c is, of course, the speed of sound.

In a preferred embodiment the columns of G describe an autoregressive model, usually of order 2. The formulations is similar to that used in that of the autoregressive change-point detector developed by Ó Ruanaidh and Fitzgerald [2]. The autoregressive model is favored in this context because it is general enough, for example, to describe a pure tone (i.e. the poles of the filter lie on the unit circle) as well as to describe multipath (i.e. through the excitation sequence). Note that G is a function of x because changing x changes the path length and the time of flight. Locating the target is equivalent to maximizing the log likelihood.

In this case, the cost function is given by the negative of the log likelihood and x can be determined using numerical optimization as described earlier.

In summary, the present invention provides a Bayesian spectral analysis that can be applied to estimate phase rapidly to a high degree of accuracy. These phase estimates are subsequently converted into target position (location) estimates using non-linear optimization of a cost function.

The present invention is a method whereby one can detect (via acoustic measurements) a frequency or multiplicity of frequencies emanating from a target and thereby estimate the location of the target. The signals can be, for example, relatively high speed longitudinal sound waves (e.g., approximately 1,500 meters/sec in breast tissue). The corresponding phase differences induced by the travel time from the target (source) to the sensor or to multiplicity of sensors may be quite small particularly at low frequencies. It is generally believed by those skilled in the art that these phase differences are too small to be of use in locating the target. Contrary to general belief, the inventors herein claim that the presented method is precise enough to yield phase estimates that can be used to reliably detect and locate a foreign object, microcalcification, calcification, or tumor.

The steps as described earlier in this invention are:
1) An optional preliminary spectral analysis step to determine frequency and/or chirp and/or other non-linear parameters contained in the regression matrix. This step is optional because these values are typically known in advance.
2) Regression to estimate the magnitude of in-phase and quadrature components. Linear regression is typically used in this step but it will be evident to those skilled in the art that robust regression can be substituted for linear regression and may yield better results in some circumstances. Moreover, we also recognize that Bayesian regression can also be applied to utilize prior information about the linear parameters.
3) Phase estimation calculated directly from the linear in phase and quadrature parameters using a standard formula.
4) Conversion of the phase estimates into a position estimate using non-linear optimization of a cost function.

The present invention also derives estimates for the phase standard deviation. This expression follows from a standard propagation-of-errors argument that would be familiar to those skilled in the art. Nonetheless, the original application of these quantities is used for objectively measuring the quality of the data gathered by a specific sensor. These figure-of-merit quantities are also useful in devising the cost function, the minimization of which yields an estimate of the location of the source of acoustic radiation.

Alternatively, one can derive a likelihood function for the received signal over the direct paths to the sensor, as a function of the target position. Maximizing the likelihood with respect to the target position would yield a so-called "maximum likelihood" estimate of the target position. In this case, the cost function (which is minimized) would be the negative of the log likelihood function.

Figure 2:
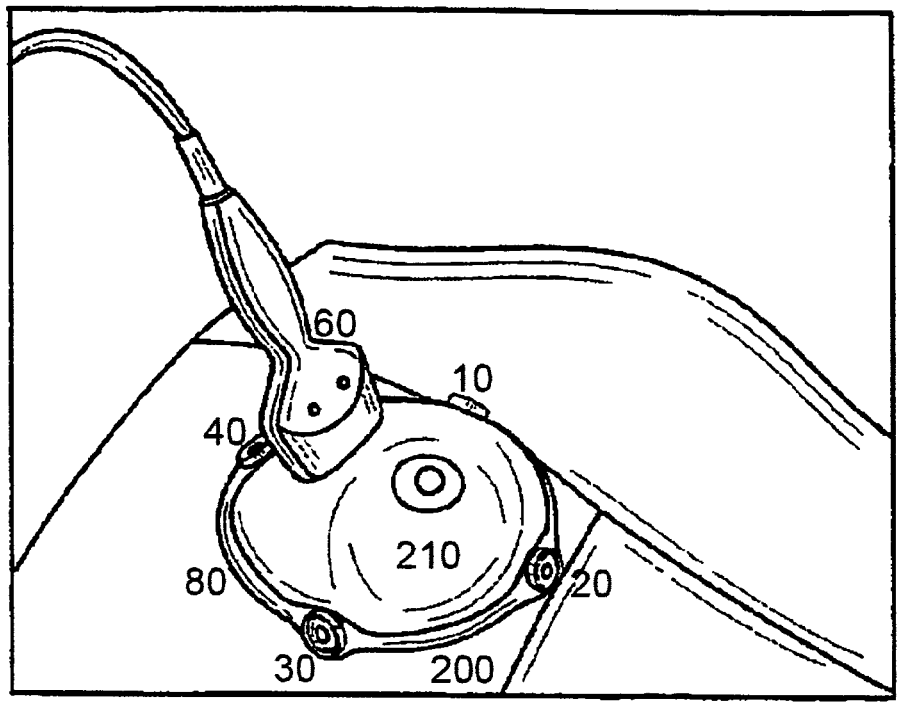
FIG. 2 is a diagram showing the orientation of the acoustic sensors housed in a sort of housing placed on or around a human breast relative to a scanning ultrasonic transmitting transducer (whether hand-held, hand-free, single element, linear array or phased-array) incrementally or wholly scanning different segments of the human breast.

As a representative example, suppose four sensors are positioned in a ring-like holder 80 on or around a breast 210 as shown in FIG. 2. The (0, 0, 0) coordinates are the chest wall 200 at the center base of the breast 210. The sensors 10, 20, 30 and 40 lie on a circle of radius 6 centimeters. The XYZ coordinates of the four sensors are (in cm) (6, 0, 0), (0, 6, 0), (−6, 0, 0) and (0, −6, 0), respectively, and a transducer 60 is placed against the breast at known coordinates (2, 3, 2).

Additionally, there is an object such as a microcalcification within the breast at position (−2, 1, 1). This position is unknown and has to be inferred from measurements of phase shifts and propagation delays.

Figure 4:
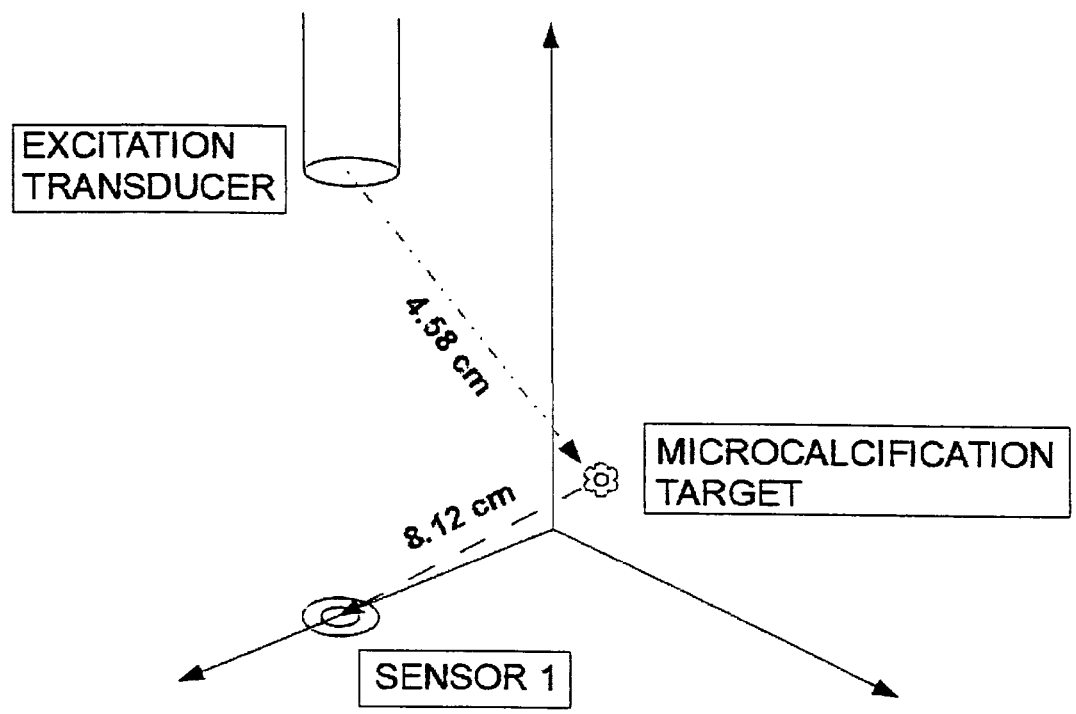
FIG. 4 is a diagram showing one hypothetical possible configuration of the transducer, sensor, and target object. If the transducer is located at coordinates (2, 3, 2) and the object is at coordinates (−2, 1, 1) then the distance between them is 4.58 cm. If the sensor is at (6, 0, 0) then the distance between the sensor and the object is 8.12 cm and the total path length from transducer to object to sensor is 4.58+8.12=12.70 cm.

The total distance from the transducer to the object and then from the object to the sensor located at (6, 0, 0) is 12.71 cm as shown in FIG. 4, and calculated using the Pythagorean Theorem as shown in Equation 13. The distance in the case of the remaining three sensors are 10.06, 8.83 and 11.93. Assuming the speed of sound is 1480 m/s, the time taken for the signal to propagate along each path (the time delay of each demodulated or reradiated signal) is 85.86, 67.97, 59.63 and 80.62 microseconds, respectively. If the transducer signal is modulated by a tone of 3 kHz and this signal is demodulated at the location of the target object as a result of its interaction with the target object, the time delays computed above would yield phase shifts in the received, demodulated, 3 kHz signal at each sensor of 92.7, 73.4, 64.4 and 87.1 degrees with respect to the transmitted transducer modulation envelope. Equation 14 shows the arithmetic involved in calculating the first of these values. Using these phase differences alone, the present inventors are able to use the methods described earlier to estimate the location of the object.

$$d_1 = \sqrt{(6+2)^2 + (0-1)^2 + (0-1)^2} + \sqrt{(-2-2^2) + (1-3)^2 + (1-2)^2}$$
$$= 8.12 + 4.58$$
$$= 12.71$$

Equation (13)

$$92.7° = 2\pi \cdot (3 \times 10^3) \cdot (85.86 \times 10^{-6}) \cdot \frac{180}{\pi}$$

Equation (14)

Figure 3:
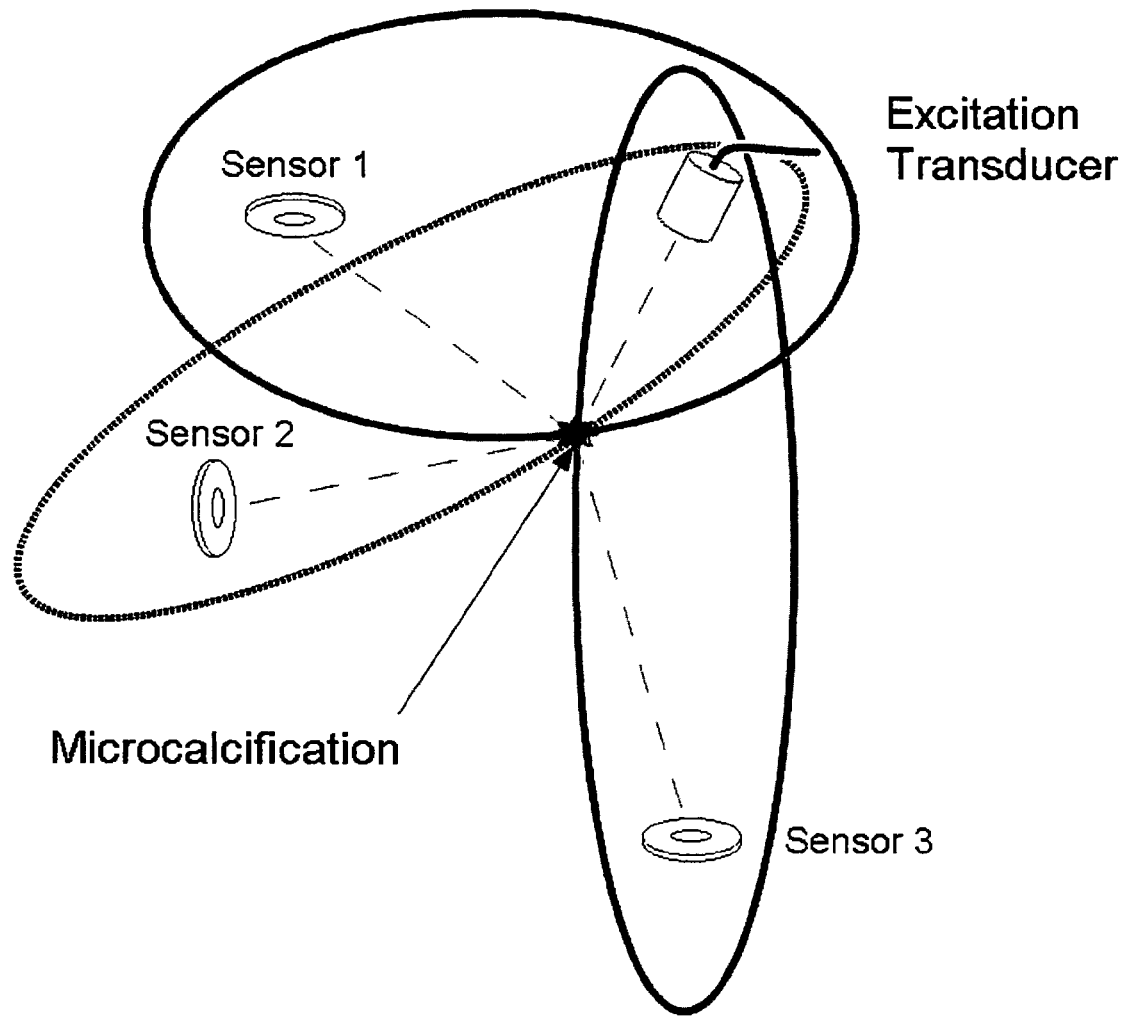
FIG. 3 is a diagram showing the mathematical equivalent of determining the location of the object. The time-of-flight multiplied by the speed of sound is the path-length travelled by the wave. One can estimate time-of-flight by determining the phase shift in the demodulated wave received by the sensor, or by observing the time difference between the leading edge of the signal received at the sensor relative to the leading edge of the transmitted signal, or by using both. Each ellipse corresponds to the set of points that have the same path-length between a given sensor and the transducer, via the target. By path-length, we mean the distance from the transducer to the target plus the distance from the target to the sensor. Given just one sensor, and the measurement of path length, all one can say is that the target is located somewhere on an ellipse, with the sensor at one focus and the transducer at the other focus. For the sake of clarity, there are three sensors and three corresponding ellipses shown in FIG. 3. The target must be located at the unique point of intersection between ALL three ellipses. We have thus located the target.

As shown in FIG. 3, determining the location of the object is mathematically equivalent to finding the point of intersection between a number of ellipsoids, each of which has one focus located at the excitation transducer, the other focus centered on a particular sensor, and a major diameter determined by the phase shift of the signal received by that sensor relative to the excitation waveform. For the sake of clarity this figure shows only the three-sensor case. This phase shift corresponds to the time between the generation of the ultrasonic excitation signal and the reception by the sensor of a signal reflected, demodulated, or reradiated by the target object.

Because of the propagation delay, there is a quiet period at the beginning before the sensors receive any signal. At a typical sampling rate of 200 kHz, the quiet period would comprise 17.17, 13.59, 11.93 and 16.12 sample periods. Therefore, the first 17, 13, 11 and 16 rows of the G matrix in this example would be composed of zeros. These are the sample delays which would maximize the log likelihood and hence locate the target.

Furthermore, the present invention method can also be used to optimize the location of the sensors. This goal can be attained by optimizing the position of the sensors with respect to a cost function. In this configuration, the true position of the signal emitting target would be known and those positions of the sensors that yield the best estimate of the true position would be considered optimal. The true position would be determined over a suitable large number of trials in which the true signal emitting target position would be chosen either judiciously, or randomly, or some combination thereof in an effort to be representative of the target location in a real-world situation (i.e., inside of a human breast).

What is claimed is:

1. A method of detecting a target in a medium, comprising:
   a) generating an ultrasound signal having a modulation envelope and causing the ultrasound signal to impact the target;
   b) demodulating the ultrasound signal having a modulation envelope through the interaction of the ultrasound signal having a modulation envelope and the target and receiving the demodulated signal by at least one sensor to determine that a detected target is present in the medium;
   c) determining a location of a detected target in one dimension from a distance of at least one sensor to the target in the medium by measuring the time-of-flight of the demodulated signal to the at least one sensor having a known location, the distance between the at least one sensor and the target being calculated by multiplying the time-of-flight by the sound speed in the medium;
   d) the at least one sensor yields at least one distance value from the signal emitting target;
   e) the modulated ultrasound signal is confined substantially to linear beam;
   f) an error function is defined for each sensor for each point along a line coincident to the modulated ultrasound beam;
   g) the error function is based on a difference between the distance determined by the sensor and the actual distance to each point along the line;
   h) a cost function is defined for each point along the line based upon a combination of the error functions for each sensor, the minimization of which estimates the position along the line of the source of radiation (i.e. the signal emitting target); and
   i) the cost function is based upon a weighted sum of the error functions for each sensor.

2. The method in accordance with claim 1 in which a phase difference between the modulation envelope of the signal transmitted by the transducer and the demodulated signal received by the at least one sensor depends on the distance of the at least one sensor to the target and, consequently, is used to determine the time of flight.

3. The method in accordance with claim 2 where the phase is determined using regression to determine the magnitude of in-phase and quadrature components and the phase is then computed using a standard formula using the magnitude of the quadrature component relative to the magnitude of the in-phase component.

4. The method in accordance with claim 3 where a Bayesian Spectral Analysis is applied to determine the frequency of a single tone.

5. The method in accordance with claim 3 where robust regression is used to determine the magnitude of the in phase and quadrature components.

6. The method in accordance with claim 3 where Bayesian regression is used to determine the magnitude of the in-phase and quadrature components.

7. The method in accordance with claim 3 where a variance of an estimate of the phases is approximated by applying propagation-of-errors techniques to a covariance matrix obtained by regression, and considering the conversion of Cartesian in-phase and quadrature coordinates to Polar coordinates comprising phase and magnitude coordinates.

8. The method in accordance with claim 1 where the weight of each error function component is given by an inverse of an estimate of a variance of a phase value measured by the respective sensor.

9. The method in accordance with claim 1 where the distance from the at least one sensor to the target are calculated based upon the phase difference between the modulation envelope of the signal transmitted by the ultrasound transducer and the signal received by the sensor.

10. The method in accordance with claim 1 where the cost function is minimized and thereby yields an estimate for the target location, and minimization of the cost function decreases as a corresponding likelihood function increases.

11. The method in accordance with claim 10 where the cost function for a distance from the at least one sensor to the target is a negative of the logarithm of a likelihood function for a distance from the at least one sensor to the target.

12. The method in accordance with claim 11 where the cost function for a multitude of distances from the at least one sensor to the target is the sum of a negative of the logarithm of the likelihood functions of the distances from the at least one sensor to the target.

13. The method in accordance with claim 11 where the likelihood function is the student-t distribution based on a model matrix; the model matrix possessing the following properties:
   (a) the matrix elements corresponding to a time of arrival before the time of flight are zero or as close to zero as possible; and
   (b) the matrix elements corresponding to a time of arrival after the time of flight are generally non-zero, and jointly describe a delayed version of the signal emitted by the ultrasound transducer.

14. The method in accordance with claim 11 where the likelihood function is the student-t distribution based on a model matrix, whose elements depend on the position of the source and hence the distance from the at least one sensor to the target length; the model matrix possessing the following properties:
   (a) the columns of the matrix elements corresponding to a time of arrival before the time of flight are zero or as close to zero as possible; and
   (b) the signal emitted by the transducer is a pure tone and the matrix elements corresponding to a time of arrival after the time of flight are generally non-zero, and the columns jointly describe a delayed version of the pure tone emitted by the ultrasound transducer.

15. The method in accordance with claim 1 further comprising: the at least one sensor is increased to at least three receiving sensors and determining a location of a detected target in three dimensions in the medium is performed by measuring the time-of-flight of the demodulated signal emitted from the target to each of the at least three receiving sensors having known locations, the distance between each of the at least three receiving sensors and the target being calculated by multiplying the time-of-flight measured by each of the at least three receiving sensors by the sound speed in the medium, and the three dimensional location being determined by applying a trilateration technique to the calculated distances.

16. The method in accordance with claim 1 further comprising: determining a location of a detected target in three dimensions in the medium by measuring the time-of-flight of the demodulated signal emitted from the target to each of the at least three receiving sensors having known locations and the three dimensional location of the target being determined by applying a multilateration technique to the time-of-flight values.

17. The method in accordance with claim 1 further comprising: the medium is a human breast.

18. The method in accordance with claim 1 further comprising: the target is selected from and used in conjunction with the group consisting of a microcalcification in the human breast tissue, a calcification in the human breast tissue, a cluster of microcalcifications in the human breast tissue and a cluster of calcifications in the human breast tissue.

19. The method in accordance with claim 1 further comprising: transmission of the demodulated signal generated by the interaction of the ultrasound signal having a modulation envelope and the target is selected from and used in conjunction with the group consisting of reflection, re-radiation and demodulation.

20. The method in accordance with claim 1 further comprising: the generated ultrasound signal is generated by a transmitting ultrasonic transducer selected from the group consisting of a single element transducer and an array transducer.

21. The method in accordance with claim 1 further comprising: the at least one sensor is selected from the group consisting one or more of: acoustic sensors, a microphone, microphones, a hydrophone, hydrophones, an accelerometer, accelerometers, a strain gauge, strain gauges, a surface microphone, surface microphones, a surface hydrophone and surface hydrophones.

22. A method of detecting a target in a medium, comprising:
   a) generating an ultrasound signal having a modulation envelope and causing the ultrasound signal to impact the target;
   b) demodulating the ultrasound signal having a modulation envelope through the interaction of the ultrasound signal having a modulation envelope and the target and receiving the demodulated signal by at least three sensors to determine that a detected target is present in the medium;
   c) determining a location of a detected target in three dimensions in the medium by measuring the time-of-flight of the demodulated signal emitted from the target to each of the at least three receiving sensors having a known location, the distance between the at least three receiving sensors and the target being calculated by multiplying the time-of-flight measured by the at least three receiving sensors by the sound speed in the medium;
   d) the three dimensional location being determined by
      d1) defining an error function for each point in space for each sensor, the sensor function being based upon the difference between the distance determined by each of the three receiving sensors and the actual distance to each point in space and
      d2) defining a cost function for each point in space based on the combination of the error functions for each of the three receiving sensors, the minimization of which estimates the location of the source of radiation (i.e. the target in three dimensions); and
   e) the cost function is a weighted sum of the cost function along the paths to more than one sensor.

23. The method in accordance with claim 22 where the weight of the error function for each point in space is given by the inverse of the estimate of the variance of the phase value measured by the respective sensor.

24. The method in accordance with claim 22 where the distances between each of the receiving sensors and the target are calculated based upon the phase difference between the modulation envelope of the signal transmitted by the ultrasound transducer and the signal received by the sensor.

25. The method in accordance with claim 22 where the cost function is minimized and thereby yields an estimate for the target location, and minimization of the cost function decreases as a corresponding likelihood function increases.

26. The method in accordance with claim 25 where the cost function for a distance from the at least one sensor to the target is a negative of the logarithm of a likelihood function for a distance from the at least one sensor to the target.

27. The method in accordance with claim 26 where the cost function for a multitude of distances from the at least one sensor to the target is the sum of a negative of the logarithm of the likelihood functions of the respective distances from the at least one sensor to the target.

28. The method in accordance with claim 26 where the likelihood function is the student-t distribution based on a model matrix; the model matrix possessing the following properties:
   (a) the matrix elements corresponding to a time of arrival before the time of flight are zero; and
   (b) the matrix elements corresponding to a time of arrival after the time of flight are generally non-zero, and jointly describe a delayed version of the signal emitted by the ultrasound transducer.

29. The method in accordance with claim 26 where the likelihood function is the student-t distribution based on a model matrix, whose elements depend on the position of the source and hence the path length; the model matrix possessing the following properties:
   (a) the columns of the matrix elements corresponding to a time of arrival before the time of flight are zero or as close to zero as possible; and
   (b) the signal emitted by the transducer is a pure tone and the matrix elements corresponding to a time of arrival after the time of flight are generally non-zero, and the columns jointly describe a delayed version of the pure tone emitted by the ultrasound transducer.

* * * * *